United States Patent [19]

Petzoldt et al.

[11] 4,196,204
[45] Apr. 1, 1980

[54] HYDROXYLATED 1 ALPHA, 2 ALPHA-METHYLENE STEROIDS

[75] Inventors: Karl Petzoldt; Hermann Steinbeck; Walter Elger, all of Berlin, Fed. Rep. of Germany

[73] Assignee: Schering Aktiengesellschaft, Berlin and Bergkamen, Fed. Rep. of Germany

[21] Appl. No.: 886,014

[22] Filed: Mar. 13, 1978

[30] Foreign Application Priority Data

Mar. 21, 1977 [DE] Fed. Rep. of Germany ....... 2712861

[51] Int. Cl.$^2$ .......................... A61K 31/58; C07J 3/00
[52] U.S. Cl. .................................. 424/243; 260/397.4; 260/347.5; 260/347.2; 260/326.33; 544/121; 544/124; 544/130; 544/141; 544/152; 544/357; 544/365; 544/372; 544/359; 544/380; 546/189; 546/194; 546/195; 546/208; 546/214; 546/263; 546/285; 546/281; 546/283
[58] Field of Search .............. 260/397.4, 347.5, 347.2, 260/326.33; 544/121, 124, 130, 141, 152, 357, 365, 372, 359, 380; 546/189, 194, 195, 208, 214, 263, 285, 281, 283; 424/243

[56] References Cited

U.S. PATENT DOCUMENTS 3,232,839  2/1966  Kieslich .............................. 424/243

*Primary Examiner*—Alan L. Rotman
*Assistant Examiner*—Robert C. Whittenbaugh
*Attorney, Agent, or Firm*—Millen & White

[57] ABSTRACT

Steroids of the formula

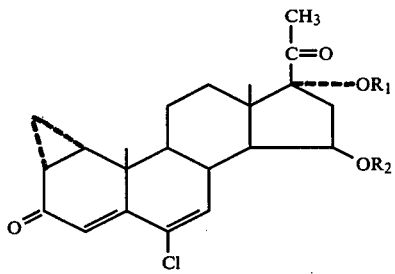

wherein $R_1$ and $R_2$ are identical or different and each is hydrogen or the residue of an organic or inorganic acid, and for the esters ($R_1$ or $R_2$ is not H) capable of salt formation, the salts thereof, possess valuable pharmacological properties, e.g., good antiandrogenic activity with low progestational activity.

29 Claims, No Drawings

HYDROXYLATED 1 ALPHA, 2 ALPHA-METHYLENE STEROIDS

BACKGROUND OF THE INVENTION

The present invention relates to pharmaceutically active 1α,2α-methylene steroids.

SUMMARY OF THE INVENTION

It is an object of this invention to provide new steroids possessing high antiandrogenic activity with minor progestational activity.

Upon further study of the specification and appended claims, further objects and advantages of this invention will become apparent to those skilled in the art.

These objects have been attained by providing hydroxylated 1α,2α-methylene steroids of Formula I

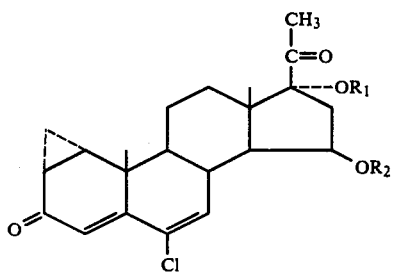

wherein $R_1$ and $R_2$ are identical or different and each is hydrogen or the residue of an organic or inorganic acid, and for the esters ($R_1$ and/or $R_2$ is not H) capable of salt formation, the salts thereof.

DETAILED DISCUSSION

To form the esters of Formula I, organic acids customarily used in steroid chemistry can be employed. Such acids include, for example, organic carboxylic and sulfonic acids of 1-18, preferably 1-12 carbon atoms. Such acids include those of the aliphatic, cycloaliphatic, aromatic, aromatic-aliphatic, or heterocyclic series, (S, O or N hetero atoms), any of which can be unsaturated and/or polybasic and/or conventionally substituted. Examples of such substituents include alkyl, hydroxy, alkoxy, oxo, amino, or halogen (F, Cl, Br, I). Although alkanoic and alkanesulfonic acids of 1-12 carbon atoms are especially preferred, contemplated equivalents are acids of all other carboxylic and sulfonic acids, e.g., short-chain hydroxycarboxylic acids of 2-6 carbon atoms esterified with further carboxylic or sulfonic acids of 2-18 carbon atoms, e.g., glycolic acid O-nonanoate, glycolic acid O-trideconoate, glycolic acid O-hexadecanoate etc. Contemplated as equivalents of the carboxylic or sulfonic acids are also those of carbocyclic aryl or alkaryl acids, e.g., containing 7-18 carbon atoms and preferably 1 or 2 rings; aralkyl acids, e.g., containing 8-18 carbon atoms, heterocyclic acids of 1 ring, e.g., containing 4-9 carbon atoms and 1-2 hetero atoms (N, O, S).

Examples of suitable carboxylic acids include: formic acid, acetic acid, propionic acid, butyric acid, isobutyric acid, valeric acid, isovaleric acid, caproic acid, enanthic acid, caprylic acid, pelargonic acid, capric acid, undecylic acid, trimethylacetic acid, diethylacetic acid, cyclopentylpropionic acid, cyclohexylacetic acid, phenylacetic acid, benzoic acid, glycolic acid, glycolic acid O-undecanoate, mono-, di-, and trichloroacetic acid, oxalic acid, malonic acid, succinic acid, adipic acid, pimelic acid, suberic acid, aminoacetic acid, diethylaminoacetic acid, diethylaminopropionic acid, piperidinoacetic acid, morpholinoacetic acid, nicotinic acid, isonicotinic acid, furan-2-carboxylic acid, and similar acids. Compounds of general Formula I also primarily include the physiologically compatible salts of the dicarboxylic acid monoesters with bases and the physiologically compatible addition salts of the aminocarboxylic acid esters with acids.

Examples of sulfonic acids suitable for ester formation include: methanesulfonic acid, ethanesulfonic acid, isopropanesulfonic acid, butanesulfonic acid, cyclopropanesulfonic acid, cyclopentanesulfonic acid, benzenesulfonic acid, p-toluenesulfonic acid, p-chlorobenzenesulfonic acid, N,N-dimethylaminosulfonic acid, N,N-diethylaminosulfonic acid, pyrrolidino-, piperidino-, piperazino-, N-methylpiperazino-, morpholinosulfonic acids, and the like. From the aminosulfonic acid esters, the physiologically compatible water-soluble acid addition salts can be produced.

Also suitable, particularly in the 15-position, are the esters of inorganic acids such as the hydrohalic (Cl, Br, I) acids, preferably sulfuric and phosphoric acids, as well as the physiologically compatible salts of the hemisulfate and monophosphoric acid esters with bases.

Physiologically compatible salts of the aforementioned bases include their alkali- and alkaline earth-metals, especially sodium salts. For the formation of the aforementioned acid addition salts, suitable physiologically compatible salts are those acids which are conventionally employed in connection with organic nitrogen compounds. Suitable such acids for salt formation include, for example, hydrochloric acid, hydrobromic acid, phosphoric acid, acetic acid, propionic acid, lactic acid, tartaric acid, succinic acid, citric acid, benzoic acid, salicylic acid, nicotinic acid, adamantanecarboxylic acid, etc.

A process for the preparation of the hydroxylated 1α,2α-methylene steroids of Formula I comprises fermenting compounds of Formula II

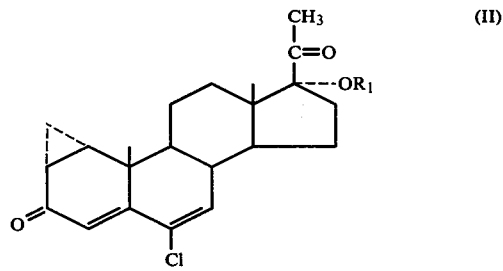

wherein $R_1$ is as defined above, with a bacterial culture of the genus Bacillus or with a fungal culture of the genus Mucor, and, esterifying any free hydroxy groups in the 17- and/or 15-positions when required to produce the desired $R_1$ and $R_2$ moieties.

When $R_1 = H$, Formula II represents the known steroid, cyproterone. The starting material cyproterone esters of Formula II can be prepared in accordance with the esterification procedures discussed below, if desired, or the corresponding esterification can be performed after the 15β-hydroxylation.

The 15β-hydroxylation is accomplished using a bacterial culture of the genus Bacillus or with a fungal culture of the genus Mucor. Suitable for this fermentation are the bacterial strain, for example, *Bacillus megaterium* (ATCC 13 368) and the fungal strain, for example, *Mucor griseocyanus* (ATCC 1207 b).

The fermentation is conducted under the same conditions employed in conventional fermentative conversions of steroids using bacterial and fungal cultures. For the fermentative conversions see W. Charney and H. L. Herzog "Microbial Transformation of Steroids", Academic Press, New York and London, 1967.

Thus, initially, the most favorable fermentation conditions are determined by conventional routine preliminary tests such as, for example, the selection of the most favorable nutrient medium; the suitable substrate solvent; the substrate concentration; the technical conditions, such as temperature, aeration conditions, pH value, etc.; and the optimum periods of germination, addition of substrate and substrate contact with the enzyme of the microorganism. These latter determinations are done analytically, especially by thin-layer chromatography.

It has been found, in this connection, that it is advantageous to utilize concentrations of about 50–1,000 mg of substrate per liter of nutrient medium. The pH value is preferably in the range of 5–7. The culturing temperature is in the range of 20°–40° C., preferably 25°–35° C., and the pressure 0–1 atm. gauge. For aeration, about 1 liter of air per minute per liter of culture broth is added. The conversion of the substrate is suitably observed by analyzing sample extracts using thin-layer chromatography. IN general, satisfactory quantities of hydroxylated steroid have formed after 50–100 hours.

After the fermentation is complete, the fermentation products are isolated conventionally. The isolation can be done, for example, by extracting the fermentation batches with a polar solvent which is not water-soluble, such as ethyl acetate, butyl acetate, or methyl isobutyl ketone; concentrating the extracts; and purifying the thus-obtained crude products optionally by chromatography and/or crystallization.

For the esterification step, conventional steroid chemistry processes can be utilized as disclosed for example in U.S. Pat. No. 4,011,314, whose disclosure is incorporated by reference herein. Since the secondary hydroxy group in the 15-position and the tertiary hydroxy group in the 17-position exhibit different reactivities, the hydroxy groups can also be esterified in stages. Moreover, it is frequently useful to start with compounds already esterified in the 17α-position, particularly if relatively drastic conditions are required for the esterification of the 15-hydroxy group, such as, for example, in the esterification with inorganic acids or when producing the aminoacylates from the corresponding chloroacylates. The partial esterification in the 15-position is preferably conducted in the presence of an alkaline catalyst at room temperature. Suitable catalytic bases are preferably tertiary amines, e.g. triethylamine, pyridine, collidine, optionally with the addition of 4-dimethylaminopyridine. Suitable esterifying agents are reactive acid derivatives, such as acid halogenides or anhydrides of monocarboxylic acids.

The esterification of the hydroxy group in the 17-position with a monocaroxylic acid may be conducted by utilizing fully conventional methods, see for example U.S. Pat. No. 3,749,742 and U.S. Pat. No. 2,753,360. One example is the reaction with the anhydride or halogenide of the desired acid in the presence of a strongly acidic catalyst, such as perchloric acid, p-toluenesulfonic acid, trifluoroacetic acid, at room temperature or in the presence of an alkaline catalyst, such as pyridine, collidine, quinoline, opitionally with the addition of 4-dimethylaminopyridine, at temperatures of from above room temperature to the boiling point of the base.

The esterification of the hydroxy groups in the 15- and 17-positions can also be effected with a free carboxylic acid in the presence of trifluoroacetic anhydride, see U.S. Pat. No. 3,383,394.

If the 3-enol ester is formed simultaneously during the acidic esterificatiion, the enol ester grouping can be selectively split off in a conventional manner, for example by treatment with mineral acids or also with paratoluenesulfonic acid in an alcoholic solution, see U.S. Pat. No. 2,753,360.

The esterification of the free hydroxy groups with dicarboxylic acids is conducted, according to a preferred embodiment, with a mixture of trifluoroacetic anhydride and the desired dicarboxylic acid. The esterification is advantageously carried out at 10°–50° C. in the presence of a solvent inert to the reactants. Suitable solvents include water-miscible solvents, such as tetrahydrofuran or dioxane, as well as water-immiscible solvents, such as benzene, see U.S. Pat. No. 3,525,755.

The water solubility of suitable salts of the compounds esterified with one or two dicarboxylic acids is of special significance. For purposes of such salt formation, the acidic monoesters are dissolved, for example, in alcohol and neutralized with the base, especially sodium hydroxide solution. A compound monoacylated in the 17-position with a carboxylic acid can be converted into the 15-sulfonic acid ester by conventionally reacting the 17-monoacyl compound in the presence of a tertiary amine with a sulfonic acid halogenide at room temperature. If a 15,17-dihydroxy compound is reacted with a sulfonic acid halogenide in the presence of a tertiary amine at room temperature, the 15,17-disulfonic acid ester is obtained.

For conducting the esterification with an inorganic acid and for the preparation of aminoacylates, compounds which have already been esterified in the 17α-position are suitably used as the starting materials. Thus, 15-hemisulfate alkali metal salts are prepared from the 15-hydroxy compounds according to methods known per se, e.g., as described in British Pat. No. 1,286,093. For example, initially, pyridine-sulfur trioxide adduct can be used to convert the 15-hydroxy compounds into the acidic 15-sulfuric acid esters, and the latter are then conventionally converted into the physiologically compatible salts with bases. Suitable bases include alkali metal hydroxides and alcoholates, especially of sodium.

The 15-aminoacylates of this invention, such as, for example, the diethylamino-, piperidino-, and morpholinoacetates, can be obtained according to known methods by reaction of the corresponding 15-hydroxy compounds with a halofatty acid anhydride or halogenide in the presence of an organic base, such as pyridine, by way of the 15-haloacylate and subsequent reaction with the desired amine, see British Pat. No. 1,286,093. Preferred amines are secondary aliphatic and cyclic amines, such as diethylamine, pyrrolidine, piperidine, piperazine, N-methylpiperazine, morpholine, etc. The reaction of the 15-haloacylate with the amine takes place simply by heating the components together. Suitably, excess amine serves as the solvent. Essentially, the reaction can also be conducted in a dilute solution. The thus-obtained 15-aminoacylates can be converted into the corresponding acid addition salts by following conventional methods.

The hydroxylated 1α,2α-methylene steroids of Formula I are pharmacologically active compounds. For example, the novel compounds possess a strong antiandrogenic activity with minor progestational activity.

To determine the antiandrogenic activity, the inhibition of the testosterone propionate caused increase in the weight of the seminal vesicles and prostates of rats was determined upon subcutaneous application. As demonstrated by the following Table 1, a compound of this invention, 17-acetoxy-6-chloro-15β-hydroxy-1α,2α-methylene-4,6-pregnadiene-3,20-dione (A) has the same strong antiandrogenic activity as the strong antiandrogen, 17-acetoxy-6-chloro-1α,2α-methylene-4,6-pregnadiene-3,20-dione (B). The antiandrogenic activity was tested on male castrated rats as described in Acta endocr. (Kbh.) Suppl. 90 (1964) 139.

TABLE 1

| Compound | Dose (mg/day) | Testosterone Propionate Inhibition | |
|---|---|---|---|
| | | Seminal Vesicle | Prostate |
| A | 1.0 | 72% | 72% |
| B | 1.0 | 73% | 74% |

In the Clauberg test after subcutaneous application to rabbits, the 15β-OH-compound A of this invention is ineffective at a dosage of 0.03 mg (McPhail=1.1). The conventional antiandrogen B is still effective at a dosage of only 0.003 mg (McPhail=1.5). The gestagenic effect was checked in the usual Clauberg test (Zbl. Gynak. Vol. 54 (1930) 2757 and J. Physiol. (London) Vol. 83 (1934) 10 and 145).

TABLE 2

| Compound | Dose (mg) | McPhail |
|---|---|---|
| A | 0.03 | 1.1 |
| B | 0.003 | 1.5 |

On the basis of such favorably opposed antiandrogenic and progestational activities, the compounds of this invention are particularly well suitable for the treatment of diseases caused by androgens or dependent on androgens in mammals, including humans. Thus, the compounds can be utilized, for example, in the form of the water-soluble ester salts for the local treatment of acne and seborrhea.

The pharmacologically active compounds of Formula I can be processed in accordance with conventional methods of galenic pharmacy to produce medicinal agents. Conventional excipients are pharmaceutically acceptable organic or inorganic carrier substances suitable for parenteral, enteral or topical application which do not deleteriously react with the active compounds. Suitable pharmaceutically acceptable carriers include but are not limited to water, salt solutions, alcohols, vegetable oils, polyethylene glycols, gelatine, lactose, amylose, magnesium stearate, talc, silicic acid, viscous paraffin, perfume oil, fatty acid monoglycerides and diglycerides, pentaerythritol fatty acid esters, hydroxymethylcellulose, polyvinyl pyrrolidone, etc. The pharmaceutical preparations can be sterilized and if desired mixed with auxiliary agents, e.g., lubricants, preservatives, stabilizers, wetting agents, emulsifiers, salts for influencing osmotic pressure, buffers, coloring, flavoring and/or aromatic substances and the like which do not deleteriously react with the active compounds.

For parenteral application, particularly suitable are solutions, preferably oily or aqueous solutions, as well as suspensions, emulsions, or implants, including suppositories. Ampoules are convenient unit dosages.

For enteral application, particularly suitable are tablets, dragees, or capsules having talc and/or a carbohydrate carrier or binder or the like, the carrier preferably being lactose and/or corn starch and/or potato starch. A syrup, elixir or the like can be used wherein a sweetened vehicle is employed.

For topical application, the compounds of this invention are employed as non-sprayable forms, viscous to semi-solid or solid forms comprising a carrier indigenous to topical application and having a dynamic viscosity preferably greater than water. Suitable formulations include but are not limited to solutions, suspensions, emulsions, creams, ointments, powders, linaments, salves, aerosols, etc., which are, if desired, sterilized or mixed with auxiliary agents, e.g., preservatives, stabilizers, wetting agents, buffers, or salts for influencing osmotic pressure, etc. For topical application, also suitable are sprayable aerosol preparations wherein the active ingredient, preferably in combination with a solid or liquid inert carrier material, is packaged in a squeeze bottle or in admixture with a pressurized volatile, normally gaseous propellant, e.g., a freon. Usually, the active compounds of the invention are incoroporated in topical formulations in a concentration of about 0.001 to 5 weight percent.

Sustained release compositions can be formulated including those wherein the active compound is protected with differentially degradable coatings, e.g., by microencapsulation, multiple coatings, etc.

Generally, the compounds of this invention are dispensed in unit dosage form comprising 10-100 mg in a pharmaceutically acceptable carrier per unit dosage.

The dosage of the compounds according to this invention is 10-500 mg/day when administered to human patients as an antiandrogenic agent. Suitable modes of administration are in the same manner as the known antiandrogenic agent B.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLE 1

A 2-liter Erlenmeyer flask containing 500 ml. of a nutrient solution of 0.1% peptone, 0.2% corn steep liquor, 0.5% glucose, and 0.5% yeast extract, sterilized for 30 minutes in an autoclave at 120° C.—adjusted to pH 7.2—is inoculated with a slanted-tube agar culture of Bacillus megaterium (ATCC 13 368) and shaken for 48 hours at 30° C. on a rotary shaker.

A 20-liter fermentor filled with 15 liters of a medium of the same composition as the shaker flask subculture, sterilized at 121° C. and under 1.1 atmospheres gauge, is then inoculated with this subculture. With the addition of several cubic centimeters of Silicone SH as an antifroth agent, the culture is germinated at 29° C. under aeration (10 l./min.), a pressure of 0.7 atm. gauge, and under agitation (220 r.p.m.) for 24 hours.

Under sterile conditions, 1.8 l. of culture broth is then withdrawn from this preliminary fermentor culture, and a 50-liter fermentor containing 28 l. of sterilized nutrient medium of the same composition as the preliminary fermentor culture is inoculated with this culture broth. The latter is germinated under the same conditions as in the preliminary fermentor (29° C., 30 l./min. of air, 0.7 atm. gauge, 220 r.p.m.). After a growth time of 12 hours, a solution of 6 g. of cyproterone acetate (17-acetoxy-6-chloro-1α,2α-methylene-4,6-pregnadiene-3,20-dione) in 45 ml. of dimethylformamide is added, and the culture is further agitated and aerated.

After a contact period of 88 hours, the optimum of conversion has been reached. The fermentor content is, at this point in time, extracted first with one-half and then once more with one-third of the volume with methyl isobutyl ketone by agitation. The extracts are combined and concentrated in a forced circulation evaporator at 28° C. under a vacuum to 1 liter. The concentrate is evaporated to dryness in the forced circulation evaporator at a bath temperature of 50° C. The residue is taken up in methanol; the undissolved silicone oil (antifroth agent) is separated, and the methanolic solution is evaporated to dryness under vacuum.

To purify the hydroxylation product and to separate unreacted starting material, the residue is chromatographed over a silica gel column and eluted with the aid of a linear gradient hexane-hexane/acetone. After crystallization from acetone/isopropyl ether, the pure 17-acetoxy-6-chloro-15β-hydroxy-1α,2α-methylene-4,6-pregnadiene-3,20-dione melts at 276°-277° C. The yield is 43%.

EXAMPLE 2

Under the culturing and fermentation conditions of Example 1, a 50-liter fermentor is prepared with 28 l. of a Bacillus megaterium culture and, after a culture period of 12 hours, combined with 6 g. of cyproterone (6-chloro-17-hydroxy-1α,2α-methylene-4,6-pregnadiene-3,20-dione), dissolved in 400 ml. of dimethyl sulfoxide. After a contact period of 60 hours, the content of the fermentor is extracted with methyl isobutyl ketone and worked up as described in Example 1. The thus-obtained crude product is chromatographed over a silica gel column with the use of the solvent gradient methylene chloride-methylene chloride/acetone and recrystallized from acetone/hexane, thus obtaining in a 36% yield pure 6-chloro-15β,17-dihydroxy-1α,2α-methylene-4,6-pregnadiene-3,20-dione, m.p. 251°-253° C.

EXAMPLE 3

(a) 40 g. of adipic acid is suspended in 300 ml. of benzene, and 120 ml. is distilled off to remove water. The mixture is then cooled to 5° C. and, at this temperature, 75 g. of trifluoroacetic anhydride is added under agitation. The reaction mixture is stirred for about 1 hour at room temperature, thus producing a clear solution.

Thereafter 14 g. of 17-acetoxy-6-chloro-15β-hydroxy-1α,2α-methylene-4,6-pregnadiene-3,20-dione is added thereto and the solution, which is now discolored to a dark brown, is agitated for 5 hours at room temperature. To work up the reaction mixture, the solution is stirred into 1 liter of ice water, stirred for 15 minutes under ice cooling, and the pH value is adjusted to pH 5 with 5 N NaOH solution. Subsequently the mixture is extracted three to five times with respectively ½ liter of ethyl acetate; the extracts are combined and concentrated to about 1 liter by evaporation under vacuum.

To purify the hemiadipate, the ethyl acetate solution is extracted five times with respectively 750 ml. of 3% NaHCO₃ solution, and the combined NaHCO₃ solutions are washed twice with respectively 300 ml. of ethyl acetate. The NaHCO₃ solution is acidified under agitation with 5 N HCl to pH 3.5-4.5 and extracted four times with respectively ½ liter of ethyl acetate. The combined ethyl acetate phases are finally washed free of adipic acid with a small amount of distilled water and dried over Na₂SO₄. Upon evaporation under vacuum, the 15-hemiadipate remains in the form of a yellow, oily residue (13.5 g.). After crystallization from ether, the pure 17-acetoxy-15β-adipoyloxy-6-chloro-1α,2α-methylene-4,6-pregnadiene-3,20-dione melts at 172°-174° C.

(b) 10.2 g. of 17-acetoxy-15β-adipoyloxy-6-chloro-1α,2α-methylene-4,6-pregnadiene-3,20-dione is dissolved in 50 ml. of ethanol, the solution is cooled to about 5° C. and adjusted to pH 8.0 at this temperature under agitation with the aid of N/10 NaOH. The mixture is then filled up with distilled water to a volume of 150 ml., 1 g. of activated carbon is added, and the mixture is agitated for 1 hour at room temperature. The mixture is then filtered twice through a folded filter, and the filtrate is distilled at a bath temperature of no higher than 30°-35° C. under vacuum until the main quantity of the alcohol has been removed. The colorless solution is then frozen in a refrigerating bath of −70° C. under rotary motion in a round flask and subjected to freeze-drying. Yield: 9.8 g. of 17-acetoxy-15β-adipoyloxy-6-chloro-1α,2α-methylene-4,6-pregnadiene-3,20-dione, sodium salt, m.p. 180°-200° C. (under decomposition).

EXAMPLE 4

Under the conditions of Example 3(a), 1.5 g. of malonic acid in benzene is reacted with 2 ml. of trifluoroacetic anhydride. After the addition of 1 g. of 17-acetoxy-6-chioro-15β-hydroxy-1α,2α-methylene-4,6-pregnadiene-3,20-dione, the mixture is stirred for 15 minutes and then poured into ice water. After adjusting the pH to 5, the mixture is extracted repeatedly with ether and the residue of the combined ether solutions, evaporated to dryness, is chromatographed over a silica gel column with the use of a linear solvent gradient methylene chloridemethylene chloride/acetone. After concentration of the main fraction, 17-acetoxy-6-chloro-15β-malonyloxy-1α,2α-methylene-4,6-pregnadiene-3,20-dione remains as a light-colored oil (665 mg.) which, after digestion, is crystallized with isopropyl ether (m.p. 185°-189° C.). The thus-obtained hemimalonate is converted analogously to Example 3(b) into the corresponding sodium salt, thus obtaining 600 mg. of 17-acetoxy-6-chloro-15β-malonyloxy-1α,2α-methylene-4,6-pregnadiene-3,20-dione, sodium salt, m.p. 193°-195° C.

EXAMPLE 5

Under the conditions of Example 3(a), 4 g. of adipic acid in 30 ml. of benzene is reacted with 5 ml. of trifluoroacetic anhydride. Then 3 g. of 6-chloro-15β,17-dihydroxy-1α,2α-methylene-4,6-pregnadiene-3,20-dione is added thereto and the mixture is agitated for 3 hours at 150° C. After the mixture has been worked up as described in Example 3(a), the thus-obtained crude product is once more chromatographed over a silica gel column (gradient: methylene chloride-methylene chloride/acetone), thus obtaining 15β-adipoyloxy-6-chloro-17-hydroxy-1α,2α-methylene-4,6-pregnadiene-3,20-dione in the form of a hemicrystalline foam (2.2 g.) melting within a range of 100°-150° C.

The thus-obtained hemiadipate is now converted into the sodium salt analogously to Example 3(b), so that 2 g. of 15β-adipoyloxy-6-chloro-17-hydroxy-1α,2α-methylene-4,6-pregnadiene-3,20-dione, sodium salt, is obtained, m.p. 160°-180° C. (under decomposition).

EXAMPLE 6

Under the conditions of Example 3(a), 2.6 g. of adipic acid in 20 ml. of benzene is reacted with 3.3 ml. of trifluoroacetic anhydride. Thereafter, 2 g. of 6-chloro-15β,17-dihydroxy-1α,2α-methylene-4,6-pregnadiene-3,20-dione is added thereto, and the mixture is stirred for 5 hours at room temperature. After the reaction mixture has been worked up as described in Example 3(a), the thus-obtained crude product is chromatographed, for purposes of further purification, once again over a silica gel column and eluted by means of the solvent gradient methylene chloride-methylene chloride/acetone and with the addition of several drops of concentrated hydrochloric acid. The main fraction is evaporated to dryness and the residue is crystallized from ether/ethyl acetate/hexane. The pure 15β,17-diadipoyloxy-6-chloro-1α,2α-methylene-4,6-pregnadiene-3,20-dione (1.3 g.) melts at 130°-140° C. under decomposition.

The thus-obtained dihemiadipate is now converted into the disodium salt analogously to Example 3(b), so that finally 1.3 g. of 15β,17-diadipoyloxy-6-chloro-1α,2α-methylene-4,6-pregnadiene-3,20-dione, disodium salt, is obtained, melting at 200° C. under decomposition.

EXAMPLE 7

500 mg. of 17-acetoxy-6-chloro-15β-hydroxy-1α,2α-methylene-4,6-pregnadiene-3,20-dione is dissolved in 20 ml. of pyridine; 10 ml. of acetic anhydride and 500 mg. of 4-dimethylaminopyridine are added thereto and the mixture is stirred for 16 hours under nitrogen at room temperature. Then the mixture is poured into ice-cooled 8% aqueous sulfuric acid, extracted with ethyl acetate, washed neutral, and evaporated under vacuum to dryness. After crystallizing the residue from ethyl acetate/isopropyl ether in the presence of activated carbon, the pure 15β,17-diacetoxy-6-chloro-1α,2α-methylene-4,6-pregnadiene-3,20-dione melts at 285°-287° C. Yield: 440 mg.

EXAMPLE 8

10 ml. of absolute pyridine is cooled to −15° C. and 0.8 ml. of sulfur trioxide is gradually added dropwise under agitation so that the internal temperature does not rise above −5° C. Into this suspension is introduced 2.5 g. of 17-acetoxy-6-chloro-15β-hydroxy-1α,2α-methylene-4,6-pregnadiene-3,20-dione in 5 ml. of pyridine. The reaction mixture is stirred for 30 minutes at room temperature, then diluted with 50 ml. of water, and finally adjusted to pH 9 with 9 ml. of 1 N NaOH. To remove the pyridine, the mixture is extracted with methylene chloride, the pH is set to 8 with 1 N NaOH, and the mixture is evaporated under vacuum. The residue is dissolved in methanol, the sodium sulfate still undissolved in filtered off, the solution is treated with activated carbon, and, after another filtering step, evaporated once again to dryness, thus obtaining 2.1 g. of sodium (17-acetoxy-6-chloro-1α,2α-methylene-3,20-dioxo-4,6-pregnadien-15β-yl) sulfate, m.p. 88°-90° C.

EXAMPLE 9

A solution of 2.5 g. of 17-acetoxy-6-chloro-15β-hydroxy-1α,2α-methylene-4,6-pregnadiene-3,20-dione in 12 ml. of pyridine is stirred at 0°-5° C. under nitrogen and combined with 1.5 g. of chloroacetic anhydride in 9 ml. of absolute ether. The mixture is stirred for another 5 hours, and the bath temperature is allowed to rise gradually to room temperature. Then 0.3 ml. of water is added, and the product is precipitated after 5-10 minutes by pouring the reaction solution into ice water. The product is vacuum-filtered and washed, in succession, with 5% hydrochloric acid, dilute sodium bicarbonate solution, and water.

The yield is 2.9 g. of a crude product. After recrystallizing twice from ether, the pure 17-acetoxy-6-chloro-15β-chloroacetoxy-1α,2α-methylene-4,6-pregnadiene-3,20-dione melts at 225°-228° C.

Under nitrogen, 1.5 g. of 17-acetoxy-6-chloro-15β-chloroacetoxy-1α,2α-methylene-4,6-pregnadiene-3,20-dione is heated to boiling with 40 ml. of diethylamine for 3 hours. After cooling to room temperature, the mixture is diluted with chloroform and evaporated under vacuum. The residue is taken up in chloroform and washed with dilute sodium bicarbonate solution and water. The solution, dried over sodium sulfate, is evaporated under vacuum, thus obtaining 1.3 g. of 17-acetoxy-15β-diethylaminoacetoxy-6-chloro-1α,2α-methylene-4,6-pregnadiene-3,20-dione as a viscous oil.

This oil is taken up in 300 ml. of ether, filtered until clear over carbon, and combined with ethereal hydrochloric acid until the reaction is acidic as determined by the Congo red indication, thus obtaining 1.6 g. of 17-acetoxy-15β-diethylaminoacetoxy-6-chloro-1α,2α-methylene-4,6-pregnadiene-3,20-dione hydrochloride, melting at about 230° C. under decomposition.

EXAMPLE 10

Analogously to Example 7, 500 mg. of 17-acetoxy-6-chloro-15β-hydroxy-1α,2α-methylene-4,6-pregnadiene-3,20-dione is reacted with enanthic anhydride and lauric anhydride, respectively. The following products are obtained:

17-acetoxy-6-chloro-15β-heptanoyloxy-1α,2α-methylene-4,6-pregnadiene-3,20-dione as an oil, and 17-acetoxy-6-chloro-15β-dodecanoyloxy-1α,2α-methylene-4,6-pregnadiene-3,20-dione as an oil, respectively.

The preceding examples can be repeated with similar success by substituting the generically and specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. Hydroxylated 1α,2α-methylene steroids of the formula

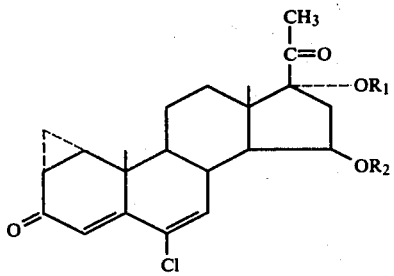

wherein $R_1$ and $R_2$ are identical or different and each is (a) hydrogen; (b) the acyl group of an unsubstituted $C_{1-18}$ alkane carboxylic or sulfonic acid; an unsubstituted $C_{6-10}$ carbocyclic aromatic carboxylic or sulfonic acid; an unsubstituted $C_{7-18}$ alkaromatic carboxylic or sulfonic acid of 1 or 2 aromatic rings; an unsubstituted $C_{8-18}$ aralkane carboxylic or sulfonic acid of 1 or 2 aromatic rings; or a piperidino, morpholino, pyridine, furan, pyrrolidino or piperazino carboxylic or sulfonic acid; (c) said acyl groups of (b) substituted by COOH, lower alkyl, OH, lower alkoxy, oxo, amino or halogen; (d) for said $C_{2-6}$ acyl groups of (c) which are substituted by OH, the corresponding acyl groups wherein the OH is esterified by a $C_{2-18}$ alkanoyl or $C_{2-18}$ alkyl sulfonyl group; (e) an esterifying group of a hydrohalic, sulphuric or phosphoric acid;

and for said 1α,2α-methylene steroids which are capable of salt formation, the physiologically acceptable salts thereof.

2. 17-Acetoxy-6-chloro-15β-hydroxy-1α,2α-methylene-4,6-pregnadiene-3,20-dione, a compound of claim 1.

3. 6-Chloro-15β,17-dihydroxy-1α,2α-methylene-4,6-pregnadiene-3,20-dione, a compound of claim 1.

4. 17-Acetoxy-15β-adipoyloxy-6-chloro-1α,2α-methylene-4,6-pregnadiene-3,20-dione, a compound of claim 1.

5. 17-Acetoxy-15β-adipoyloxy-6-chloro-1α,2α-methylene-4,6-pregnadiene-3,20-dione, sodium salt, a compound of claim 1.

6. 17-Acetoxy-6-chloro-15β-malonyloxy-1α,2α-methylene-4,6-pregnadiene-3,20-dione, a compound of claim 1.

7. 17-Acetoxy-6-chloro-15β-malonyloxy-1α,2α-methylene-4,6-pregnadiene-3,20-dione, sodium salt, a compound of claim 1.

8. 15β-Adipoyloxy-6-chloro-17-hydroxy-1α,2α-methylene-4,6-pregnadiene-3,20-dione, a compound of claim 1.

9. 15β-Adipoyloxy-6-chloro-17-hydroxy-1α,2α-methylene-4,6-pregnadiene-3,20-dione, sodium salt, a compound of claim 1.

10. 15β,17-Diadipoyloxy-6-chloro-1α,2α-methylene-4,6-pregnadiene-3,20-dione, a compound of claim 1.

11. 15β,17-Diadipoyloxy-6-chloro-1α,2α-methylene-4,6-pregnadiene-3,20-dione, disodium salt, a compound of claim 1.

12. 15β,17-Diacetoxy-6-chloro-1α,2α-methylene-4,6-pregnadiene-3,20-dione, a compound of claim 1.

13. Sodium (17-acetoxy-6-chloro-1α,2α-methylene-3,20-dioxo-4,6-pregnadien-15β-yl) sulfate, a compound of claim 1.

14. 17-Acetoxy-6-chloro-15β-chloroacetoxy-1α,2α-methylene-4,6-pregnadiene-3,20-dione, a compound of claim 1.

15. 15-Acetoxy-15β-diethylaminoacetoxy-6-chloro-1α,2α-methylene-4,6-pregnadiene-3,20-dione, a compound of claim 1.

16. 17-Acetoxy-15β-diethylaminoacetoxy-6-chloro-1α,2α-methylene-4,6-pregnadiene-3,20-dione hydrochloride, a compound of claim 1.

17. 17-Acetoxy-6-chloro-15β-heptanoyloxy-1α,2α-methylene-4,6-pregnadiene-3,20-dione, a compound of claim 1.

18. 17-Acetoxy-6-chloro-15β-dodecanoyloxy-1α,2α-methylene-4,6-pregnadiene-3,20-dione, a compound of claim 1.

19. A compound of claim 1, wherein the acid is a $C_{1-18}$ organic carboxylic or sulfonic acid.

20. A compound of claim 1, wherein the acid is sulfuric or phosphoric acid.

21. A compound of claim 1, wherein the acid is formic acid, acetic acid, propionic acid, butyric acid, isobutyric acid, valeric acid, isovaleric acid, caproic acid, enanthic acid, caprylic acid, pelargonic acid, capric acid, undecylic acid, trimethylacetic acid, diethylacetic acid, cyclopentylpropionic acid, cyclohexylacetic acid, phenylacetic acid, benzoic acid, glycolic acid, glycolic acid O-undecanoate, mono-, di-, and trichloroacetic acid, oxalic acid, malonic acid, succinic acid, adipic acid, pimelic acid, suberic acid, aminoacetic acid, diethylaminoacetic acid, diethylaminopropionic acid, piperidinoacetic acid, morpholinoacetic acid, nicotinic acid, isonicotinic acid, furan-2-carboxylic acid, methanesulfonic acid, ethanesulfonic acid, isopropanesulfonic acid, butanesulfornic acid, cyclopropanesulfonic acid, cyclopentanesulfonic acid, benzenesulfonic acid, p-toluenesulfonic acid, p-chlorobenzenesulfonic acid, N,N-dimethylainosulfonic acid, N,N-diethylaminosulfonic acid or pyrrolidino-, piperidino-, piperazino-, N-methylpiperazino- or morpholinosulfonic acid.

22. A compound of claim 1, which is an acid addition salt of an aminocarboxylic or sulfonic acid moiety in the $R_1$ or $R_2$ positions; or a basic salt of a dicarboxylic acid monoester moiety in the $R_1$ or $R_2$ positions.

23. A compound of claim 1, which is a basic salt of a hemisulfate or monophosphoric acid ester moiety in the $R_1$ or $R_2$ positions.

24. A pharmaceutical composition comprising an antiandrogenically effective amount of a compound of claim 1 and a pharmaceutically acceptable carrier.

25. A method of treating androgenic diseases in mammals which comprises administering to a mammal an antiandrogenically effective amount of a compound of claim 1.

26. The method of claim 25 wherein the disease is acne or seborrhea.

27. The pharmaceutical composition of claim 24, wherein the amount of antiandrogenic compound is 10-100 mg.

28. The pharmaceutical composition of claim 24, wherein the amount of antiandrogenic compound is 0.001 to 1 wt.%.

29. The pharmaceutical composition of claim 24, wherein the carrier is viscous to semi-solid or solid in consistency.

* * * * *